United States Patent [19]

Witkowski et al.

[11] 4,211,771

[45] Jul. 8, 1980

[54] TREATMENT OF HUMAN VIRAL DISEASES WITH 1-B-D-RIBOFURANOSYL-1,2,4-TRIAZOLE-3-CARBOXAMIDE

[76] Inventors: Joseph T. Witkowski, 5 Martha Dr., Morris Township, Morris County, N.J. 07960; Roland K. Robins, 1131 Doven Dr., Provo, Utah 84602

[21] Appl. No.: 877,313

[22] Filed: Feb. 13, 1978

Related U.S. Application Data

[60] Continuation-in-part of Ser. No. 690,912, May 28, 1976, abandoned, which is a continuation-in-part of Ser. No. 617,432, Sep. 29, 1975, Pat. No. 3,976,545, which is a division of Ser. No. 340,332, Mar. 12, 1973, Pat. No. 3,927,216, which is a continuation-in-part of Ser. No. 240,252, Mar. 31, 1972, Pat. No. 3,798,209, which is a continuation-in-part of Ser. No. 149,017, Jun. 1, 1971, abandoned.

[51] Int. Cl.$^2$ .................... A61K 31/41; A61K 31/70; C07H 19/12
[52] U.S. Cl. ........................................ 424/180; 536/23
[58] Field of Search .......................... 424/180; 536/23

[56] References Cited

U.S. PATENT DOCUMENTS

| | | | |
|---|---|---|---|
| 3,897,415 | 7/1975 | Robins et al. | 536/23 |
| 3,984,396 | 10/1976 | Witkowski et al. | 536/23 |

*Primary Examiner*—Johnnie R. Brown

[57] ABSTRACT

The compound 1-B-D-ribofuranosyl-1,2,4-triazole-3-carboxamide is used to treat diseases in humans which are caused by viral infections.

20 Claims, No Drawings

TREATMENT OF HUMAN VIRAL DISEASES WITH 1-B-D-RIBOFURANOSYL-1,2,4-TRIAZOLE-3-CARBOXAMIDE

CROSS REFERENCE TO RELATED APPLICATIONS

This application is a continuation-in-part of application Ser. 690,912 filed May 28, 1976, now abandoned which in turn is a continuation-in-part of application Ser. No. 617,432 filed Sept. 29, 1975, now Pat. 3,976,545, which in turn is a division of application Ser. No. 340,332 filed Mar. 12, 1973, now U.S. Pat. No. 3,927,216, which in turn is a continuation-in-part of application Ser. No. 240,252 filed Mar. 31, 1972, now U.S. Pat. No. 3,798,209, which in turn is a continuation-in-part of application Ser. No. 149,017 filed June 1, 1971, now abandoned. The disclosures of all of these applications are herein incorporated by reference.

BACKGROUND OF THE INVENTION

Viral infections are known to be one of the most frequent causes of human illness. Upwards of 300 different immunologic types of virus have been associated with humans; however, not all of these are identified with clinical recognizable diseases.

Many of these diseases, having once been acquired, render their host free from further infections by the same agent by stimulating a life-long immunologic response by the host to the viral agent. It is by this very same mechanism that conquest of certain virus-caused disease states has been achieved. By using prophylaxis induced by either killed or attenuated viruses or infection with an immunologically related virus which causes a very mild disease state, vaccines have been developed, for smallpox, yellow fever, polio, and some of the common childhood diseases, e.g. mumps, rubella, and measles.

While prophylaxis from some viral diseases can be obtained by immunity, immunologic protection from other viral diseases is not possible because either prolonged immunity is not developed against the virus, or the same clinically described disease is caused by a large group of related viruses which are antigenically dissimilar and do not produce cross immunity, e.g., common cold viruses.

Coupled with this lack of universal prophylaxis against all viral diseases is the necessity to effect a cure in an already established viral disease. In search for this cure of viral diseases, several chemotherpeutic agents have been used. Included in this group are amantadine (1-adamantanamine), methisazone (1-methylisatin B-thiosemicarbazone), cytarabine (cytarabine (cytosine arabinoside), 5-IDU (5-iodo-2'-deoxyuridine); however, these agents are of either limited spectrum, e.g., amantadine is only active against Type A influenze virus, cytarabine and 5-IDU are not active against RNA viruses and they are quite toxic.

SUMMARY OF THE INVENTION

The compound 1-B-D-ribofuranosyl-1,2,4-triazole-3-carboxamide has been shown to exhibit wide spectrum antiviral activity both in vitro and in vivo. The present invention relates to the use of this compound in treating diseases in humans which are caused by these very same viral agents. Accordingly, to treat viral-caused diseases in human patients, the antiviral properties of the compound 1-B-D-ribofuranosyl-1,2,4-triazole-3-carboxamide are utilized by administering to the human patient either by injection, orally, topically, ophthalmically, or via sprays or aerosols in the respiratory tract, and effective chemotherapeutic amount of the compound 1-B-D-ribofuranosyl-1,2,4-triazole-3-carboxamide.

Detailed Description of the Invention

In our sequentially co-pending applications Ser. Nos. 690,912 filed May 28, 1976, 617,432 filed Sept. 29, 1975; 340,322 filed Mar. 12, 1973; 240,252 filed Mar. 31, 1972; and 149,017 filed June 1, 1971, the disclosures of which are herein incorporated by reference, we disclosed the compound 1-B-D-ribofuranosyl-1,2,4-triazole-3-carboxamide as an antiviral agent. This compound was described as exhibiting wide spectrum antiviral activity both in vitro and in vivo. Also included in our specification as filed in applications Ser. Nos. 240,252 and 149,017, supra, was the association of some of these viruses with human viral diseases.

Viruses are classified according to the type of nucleic acid they contain. The RNA viruses contain ribonucleic acid and the DNA viruses contain deoxyribonucleic acid. Further subdivision is made into groups based upon physical and biochemical properties. The classification of a few of the viruses however, remains vague and is subject to change based upon further elucidation of their properties.

Using the taxonomic classification of C. Andrewes and H. G. Pereira, *Viruses of Vertebrates,* Third Edition, 1972, The Williams and Wilkins Co., Baltimore, the RNA viruses are subdivided into the groups Picornavirus, Reovirus, Unclassified Arbovirus, Orthomyxovirus, Paramyxovirus, Arenavirus, Rhabdovirus, Coronavirus, Togavirus, and Leukovirus. The Picornaviruses can then be further divided into two subgroups, the Enteroviruses and the Rhinoviruses. The Enterovirus subgroup includes poliovirus, coxsackie virus, and echovirus. The Arbovirus classification is a broad classification based upon association with arthprods which serve as vectors in transmission of the virus to other species. Many viruses originally classified as Arbovirus are now classified as Togaviruses and Rhabodoviruses. The Orthomyxovirus group includes influenza viruses A, B, and C. The Paramyxovirus group includes mumps virus, measles virus (i.e., rubeola), respiratory syncytial virus, and para-influenzas viruses 1, 2, 3 and 4. The Rhabdovirus group includes rabies virus. Rubella is an unclassified RNA virus.

The DNA viruses are subdivided into groups as Papovavirus, Adenovirus, Herpesvirus, Poxvirus, Iridovirus, and Parvovirus. In the Herpes group, viruses which infect man include herpes hominis Types 1 and 2, Epstein-Barr virus, varicella, and cytomegalovirus. Among the Poxviruses are variola, vaccinia, and mulluscum contagiosum.

The classification of other viruses is unsettled, including infectious and serum hepatitis and roseola infantum.

Representatives from all of the major taxonomic groups of viruses, except the RNA Leukovirus and the DNA Paravovirus and Iridovirus groups, have been associated with viral disease in humans.

Among the diseases associated with the Enteroviruses are: nonspecific febrile illness, upper respiratory infections including rhinitis, pharyngitis, conjunctivitis, and lymphonodular pharyngitis; herpangina, acute laryngotracheo bronchitis, pneumonitis and pleuritis, aseptic meningitis, epidemic pleurodynia, pericarditis, myocarditis, congenital heart disease, gastroenteritis, orchitis, lymphadenitis, and poliomyelitis. The Rhinoviruses are associated with coryza and bronchitis in children while the Coronaviruses are associated with coryza. The Rhabdoviruses are associated with rabies and vesicular stomatitis while the Arenoviruses include lymphocytic choriomeningitis and zoonotic and epidemic hemorrhagic fevers. The Togoviruses and other Arboviruses are associated with numerous fevers, encephalitis and hemorrhagic fevers including eastern, western, and Venezuelan equine encephalitis, St. Louis and California encephalitis, yellow fever and dengue. The Reoviruses are the cause of many asymptomatic infections and Colorado tick fever. Orthomyxoviruses are the causal agents of influenza. The Paramyxoviruses are associated with bronchitis, bronchiolitis, or bronchopneumonia in children, rhintis and pharyngitis in adults and other acute febrile respiratory infections, laryngotracheobronchitis, rubeola, and parotiditis. Rubella is caused by an as yet unclassified RNA virus. The Adenoviruses are associated with acute respiratory infections, pharyngo conjunctival fever, febrile pharyngitis, infant viral pneumonia, kerato conjunctivitis, and acute follicular conjunctivitis. The Herpesviruses are associated with varicella, herpes zoster, herpes genitalis, herpes labialis, acute gingivostomatitis, herpetic keratoconjunctivitis, eczema herpeticum, traumatic herpes, meningoencephalitis, infectious mononucleosis, and cytomegalic inclusion disease. The Poxviruses are associated with vaccinia, smallpox, mulluscum contagiosum, and milers nodes. The Papovaviruses are associated with warts. Uncharacterized are the infective agents of the diseases roseola infantum, hepatitis A and B, Creutfeldt-Jakob disease, kuru disease, subacute sclerosing panencephalitis and progressive multifocal encephalopthy.

For the purposes of further illustrating the invention, 1-B-D-ribofuranosyl-1,2,4-triazole-3-carboxamide will be referred to interchangeably as (a) the compound, (b) Ribavirin (nonpropriety name adopted by the United States Adopted Names Council), or (c) under its chemical name above.

The compound can be administered to the human patient by injection, orally, topically, ophthalmically, or via the respiratory tract in acrosols or drops. For systemic use the compound would be given in an amount such that the total daily dose of the compound is from about 50 milligrams to about 2500 milligrams. The normal preferred range is from about 8.5 to 20 milligrams per kilogram of body weight per day. Depending on the mode of administration, the compound can be formulated with appropriated diluents to form solutions, suspension, tablets, capsules, or syrups. For topical and ophthalmic use, the compound can be formulated with the appropriate diluents and carriers to form ointments, creams, foams, and solutions having from about 0.01% to about 15% by weight, preferably from about 1% to 10% by weight of the compound. In any event, the actual amount should be sufficient to provide a chemotherapeutically effective amount of the compound to the patient, all of which will be readily within the ability of those skilled in the art to determine given the disclosure herein.

The compounds can be administered directly into the upper respiratory tract of humans by conventional nose drops or insufflated into either the upper or both upper and lower respiratory tracks via aerosol nasal sprays or chambers and tents equipped with aerosol devices or other conventional inhalation nebulizers or vaporizers.

By way of illustration only, a specific nasal drops formulation would contain for each 1000 milliliters:

| | |
|---|---|
| 1-B-D-ribofuranosyl-1,2,-4-triazole-3-carboxamide | 20.0 g |
| Monobasic Sodium Phosphate USP XIX | 0.5421 g |
| Dibasic Sodium Phosphate USP XIX | 0.8655 g |
| Sodium Chloride USP XIX | 8.50 g |
| Benzalkonium Chloride USP XIX | 0.10 g |
| EDTA $Na_2$ | 0.05 g |
| Bidistilled Water | g.s. to |
| Phenylethyl Alcohol | 2 ml |

For nasal aerosol application the compounds may be used in an aerosol nasal spray, of the type described in U.S. Pat. No. 3,014,844, the disclosure of which is incorporated by reference herein, containing the indicated quantity of the compound suspended in a liquified propellant, such as a lower alkane (up to 5 carbon atoms), a lower alkyl chloride, or a fluorinated or fluorochlorinated lower alkane (available commercially under the trademark "Freon"). Generally, the propellant is a gas at room temperature and atmospheric pressure, has a boiling point below about 65° F. at atmospheric pressure, and of course, is non-toxic. Particularly suitable as such propellants are dichlorodifluoromethane ("Freon 12"), dichlorotetrafluoroethane ("Freon 14"), and trichloromonofluoromethane ("Freon 11"). When used in the suspension, the compound should be finely divided, as for example, smaller than 100 microns diameter, preferably not greater than 25 microns and more preferably about 0.5 to 4 microns diameter. It may also be advantageous to include a surface active agent, preferably non-ionic, e.g., esters or partial esters of fatty acids containing 6 to 22 carbon atoms such as caproic, octoic, lauric, palmitic, stearic, linoleic, etc., to help avoid agglomeration of the powder. Normally, only a relatively small quantity of the surface active agent will be used, as for example, from about 0.25 to about 1.0%, although larger quantities may be used if desired. Similarly, the stated quantity of the antiviral agent compound may be dissolved in the liquified propellant with the aid of an appropriate solvent, as described in U.S. Pat. No. 2,868,691, the disclosure of which is also incorporated by reference herein.

By way of illustration only, a specific nasal aerosol formulation would contain:

| | %W/W |
|---|---|
| 1-B-D-ribofuranosyl-1,2,4-triazole-3-carboxamide | 5.0 |
| Sorbitan Trioleate | 1.0 |
| "Freon 11" | 25.0 |
| "Freon 14" | 25.0 |
| "Freon 12" | 44.0 |
| Water, USP | — |
| Alcohol, USP | — |
| Dimethyl Ether | — |
| Valve | 50ul Susp. |
| Shot weight | 65.7 mg. |
| Assay, % W/W | 4.8 |
| Particle size range | 3–10u |

The compound can also be dissolved or suspended in a suitable solvent and be administered as an aerosol using a propellant other than a halogenated hydrocarbon, from an aerosol package equipped with a self-metering valve, all of which is known to those skilled in the art. For use in an aerosol chamber, a chamber equipped with an atomizer such as a Collison atomizer is used. This allows continuous treatment with small particle aerosols of the compound. Generally in all aerosol applications, the use of particle sizes of from about 1.0 to about 4 μm in diameter allows the compound to be deposited deep in the bronchial tree and in the alveolar spaces.

For injection the compound would be in the form of a solution or suspension. The compound would be dissolved or suspended in physiological saline or other physiologically compatible solution from about 10 to about 1500 milligrams of compound per milliliter of solution.

By way of illustration only, two formulations of different concentrations would contain for each 1000 milliliters:

| 20% Injectable | | |
|---|---|---|
| 1-B-D-ribofuranosyl-1,2,4-triazole-3-carboxamide | 200.00 | g |
| EDTA $Na_2$ | 0.05 | g |
| Sodium Benzoate | 150.00 | g |
| Benzoic Acid | 2.60 | g |
| Benzyl Alcohol | 10 | ml |
| Bidistilled Water q.s.f. | | |
| 10% Injectable | | |
| 1-B-D-ribofuranosyl-1,2,4-triazole-3-carboxamide | 100.00 | g |
| EDTA $Na_2$ | 0.05 | g |
| Methyl Paraben | 2.00 | g |
| Benzyl Alcohol | 5 | ml |
| Bidistilled Water | | |

An injectionable solution also can be prepared which contains only the compound and a suitable physiological buffer. When prepared in a sterile manner and sealed into sterile vials, no preservatives are needed. An illustration of such an injectable containing 10% by weight of compound per volume, buffered at pH 5–5 would contain:

| | | |
|---|---|---|
| 1-B-D-ribofuranosyl-1,2,4-triazole-3-carboxamide | 150.00 | g |
| Sodium Phosphate dibasic anhydrous | 553.5 | mg |
| Potassium phosphate monobasic | 13.077 | gm |
| Water USP q.s. ad. | 1500 | ml |

For use in the eye the compound would be as an ophthalmic solution or suspended in an ophthalmic ointment such as LacriLube (trademark Allergan Pharmaceuticals).

By way of illustration only, a specific ophthalmic solution formulation would contain for each 1000 milliliters:

| | | |
|---|---|---|
| 1-B-D-ribofuranosyl-1,2,4-triazole-3-carboxamide | 20.00 | g |
| Monobasic Sodium Phospate | 0.5421 | g |
| Dibasic Sodium Phosphate | 0.8655 | g |
| Sodium Chloride | 8.500 | g |
| Benzalkonium Chloride | 0.100 | g |
| EDTA $Na_2$ | 0.050 | g |
| Benzyl Alcohol | 2 | ml |
| Bidistilled Water q.s.f. | | |

The compound may be administered as an oral preparation, in either capsule, tablet, oral suspension, or syrup form. The tablets or capsules will contain from about 10 to 500 milligrams of the compound per tablet or capsule. The required dose of the compound will vary upon the condition of the patient, but will normally range from approximately 50 to 1000 milligrams per day. The capsules will be the usual gelatin capsules and will contain in addition to the compound in the quantity indicated above, a small quantity, for example less than 5% by weight, magnesium stearate or other excipient, such as "Avicel" (micro-crystalline cellulose). Tablets will contain the foregoing amount of the compound and a binder, which may be a gelatin solution, a starch paste in water, polyvinyl pyrilidone, polyvinyl alcohol in water, etc., with a typical sugar coating.

The syrup will contain from about 50 mg to 200 mg per 5 milliliters of syrup.

By way of illustration only, specific formulations for tablets, capsules, and syrup would contain:

| | | |
|---|---|---|
| For 1,000 tablets: | | |
| 1-B-D-ribofuranosyl-1,2,4-triazole-3-carboxamide | 200 | g |
| Starch USP | 146 | g |
| Polyvinyl Pyrilidine USP | 4 | g |
| Encompress | 20 | g |
| Pre-gelatinized Starch USP | 20 | g |
| Magnesium Stearate USP | 4 | g |
| Aerosil USP | 2 | g |
| Talc USP | 4 | g |
| and for each capsule: | | |
| 1-B-D-ribofuranosyl-1,2,4-triazole-3-carboxamide | 100.0 | |
| Cellulose, Microcrystalline | 122.75 | |
| Magnesium Stearate | 2.25 | |
| Total Weight | 225.00 | |
| and for 1000 milliliters of syrup: | | |
| 1-B-D-ribofuranosyl-1,2,4-triazole-3-carboxamide | 20.00 | g |
| Sorbitol 70% USP | 400 | cc |
| Ethylparaben USP | 0.9 | g |
| Propylparabene USP | 0.3 | g |
| EDTA.2Na USP | 0.01 | g |
| Sodium Chloride USP | 3.0 | g |
| Ponceau 4R (C.I. 16,255) (Martindale 26) | 0.01 | g |
| Essence of Framboesa (Firmench" 50,954 | 2 | cc |
| Propylene Glycol USP | 50 | cc |
| Alcohol 96% USP | 10 | cc |
| Demineralized Water Q.S.P. | 1000 | cc |

The compound is administered topically in an ointment, cream, emulsion, foam, or topical solution, depending on the condition of the viral skin infection to be treated. The compound is formulated with the standard carriers and other ingredients commonly used for such topical applications. Thus, ointments, by reason of a greasy base, are recommended for chronic conditions, while creams, emulsions, and topical solutions are recommended for acute and subacute lesions. Unlike ointments, creams are generally water soluble and exhibit vanishing properties. "Topical solution" refers to a solution of active ingredients in a solvent material intermediate in viscosity between creams and easily evaporable solvents like alcohol, so that a balance of spreadability and prolongation of action is achieved.

As exemplary of the many topical ointment, cream, and solution formulations which may be generally applied are the following combinations of materials:

Ointments a. Petroleum with excipients.

b. Plastibase, a plasticized hydrocarbon gel available from Squibb, Inc. and comprised of polyethylene and mineral oil.

Creams a. Methyl paraben USP
Propyl paraben USP
Spermaceti USP

Sodium lauryl sulfate USP
Stearyl alcohol USP
Cotyl alcohol USP
Glycerin USP
Deionized water
b. Stearic acid
Propylene glycol
Sorbitan monostearate and oleate
Polyoxyethylene sorbitan monostearate
Citric acid
Methyl and propyl parabens
c. Water base
Potassium sorbate
Methyl and propyl parabens
Glycerol monostearate
Squalane
Polysorbate 80 USP
Spermaceti
Stearyl alcohol
Sorbital solution
d. Polyethylene glycol 400 USP
Propylene glycol
Carboxymethylene
Monoamylamine
Titanium dioxide
Butylated hydroxytoluene Topical Solutions a. Polyvinyl alcohol-water
b. Polyethylene glycol 400

Accordingly, then, the topical vehicles are commonly comprised of, in addition to bodying agents, humectants, saponifying agents, emulsifiers, solvents, penetrants, pH regulators, plasticizers, emollients, preservatives, hardening agents, pigments, and perfumes, all as is well known in the art.

For employment against vaginal infections, topical carriers affording maximum distribution of the active agent are preferred. Thus, the compound is formulated into creams, tablets, gels, foams, and suppositories.

As exemplary of the many vaginal carriers with which the compound can be formulated are the following:

Vaginal Creams a. Glycerol monostearate
Corn oil
Glycerine
Benzoic acid
Glutamic acid
Water
b. Glycerine
Ethyl alcohol
Liquid petrolatum
Polyethylene glycol ether: fatty alcohol complex
Paraben preservatives Vaginal Suppositories a. Lactose
Polyethylene glycol 400
Polysorbate 80
Polyethylene glycol 4000
Glycerine
Lactic acid
b. Polyethylene glycol
Polyoxyethylene palmitate
Lactic acid By way of illustration only, a specific vaginal tablet formulation contain for each tablet:

| | |
|---|---|
| 1-B-D-ribofuranosyl-1,2,4-triazole-3-carboxamide | 250 mg |
| Lactose USP | 510 mg |
| Starch USP | 100 mg |
| FD&C Yellow #5 15% aluminum lake | 2.0 mg |
| Pobidone M.S. 26-28 | 25 mg |
| Alcohol spag-lg    Quantity sufficient | |
| Starch USP | 70 mg |
| Magnesium Sterate USP | 50 mg |
| Talcum USP | 10.0 mg |
| Total | 972 mg |

Topical vehicles for vaginal applications are pH-adjusted to the acid conditions under which normal bacteria flourish, so as not to debilitate body defense mechanisms. The art-skilled, of course, are well aware of this and other considerations involved in topical deployment of chemotherapeutic agents.

The topical preparations contain effective virus inhibiting proportions of the compound, e.g., from about 0.01% to about 15% by weight of the total weight of the composition, preferably 2.5% to 5% by weight. Up to about 15% by weight may be employed in the treatment of recalcitrant conditions. The quantity of the other ingredients in such preparations, of course, are commensurate with the quantities of such ingredients as normally used and determination of appropriate formulations is readily within the ability of the art-skilled given the disclosure herein.

By way of illustration only, specific topical formulations would contain for each 100 g of such formulation:

| a. | |
|---|---|
| 1-B-D-ribofuranosyl-1,2,4-triazole-3-carboxamide | 5.000 g |
| Povidone NF 13" | 2.000 g |
| Methylparaben USP 18 | 0.075 g |
| Propylparaben USP | 0.025 g |
| Xalifin 15 | 20.000 g |
| Purified Water | 72.900 g |
| b. | |
| Stearic Acid USP XIX | 18.0 g |
| White Bees Wax USP XIX | 2.0 g |
| Polyethylenglycol -400 Monostearate | 5.0 g |
| Polyethylenglycol -1000 Monostearate | 8.0 g |
| BHT Butylated Hydroxytoluene USP XIX | 0.1 g |
| Silicone Q - 2 - 2523 "Dow" | 0.5 g |
| 1-B-D-ribofuranosyl-1,2,4-triazole-3-carboxamide | 5.0 g |
| Glycerin USP XIX | 0.5 g |
| Methyl Paraben USP XIX | 0.09 g |
| Propyl Paraben USP XIX | 0.03 g |
| Phenylethyl Alcohol | 0.1 ml |
| Distilled Water | 60.2 g |
| Total weight | 90.0 g |

It should be noted that the form in which the compound is administered, of course, will depend upon the particular virus infection being treated. For example, if the infection is caused by influenza or parainfluenza and has manifested itself in the upper respiratory tract, the mode of treatment could be the described nasal drops or aerosol nasal spray since this would deliver most effectively the agent to the site of the infection, or oral or injection therapy may be indicated, depending on the severity of the infection. A lower respiratory infection might also be treated orally or by injection. If the injection is of a topical nature, such as herpes labialis (cold sore, fever blister), herpes genitalis (viral infection of the penis or of the vaginal area), herpes zoster (shingles), varicella (chickenpox), Eczema herpeticum, etc., the appropriate application would be by topical application as described above, possible combined with oral treatment or injection therapy, also as described above.

EXAMPLE 1

Varicella (chickenpox)

Eighteen patients between the ages of 7 months and 5 years were treated with Ribavirin. The parameters use for the clinical diagnosis of varicella were:
(a) Maculopapulosar eruption in different stages of development.
(b) Primary lesions which appeared on the trunk.
(c) Palms which were not vesiculated.

The drug was given orally in capsules in individualized doses ranging from 10 to 20 mg/kg of body weight per day for 5 days. Two patients also had pneuonitis as a complication. Fever and general discomfort was abated within 12 hours and involution of the lesions was seen before 48 hours. After 72 hours all of the patients became asymptomatic as opposed to a customary time period of 8 to 10 days.

EXAMPLE 2

Parotiditis (mumps)

Sixteen patients between the ages of 2 and 12 years were treated with Ribavirin. The parameter for establishing the clinical diagnosis of mumps was painful tumescence of the parotid glands. Of the sixteen cases, twelve involved bilateral swelling. No complications were noted. The drug was administered as per Example 1. Twelve hours following the initial treatment the painful swelling of the glands improved. Disappearance of the condition was noted within 24 hours in four cases and within 72 hours for the remainder.

EXAMPLE 3

Pharyngotonsillitis and Bronchopneumonia

Five patients between the ages of 8 to 12 months, four with pharyngotonsillitis and one with bronchopneumonia, all of suspected viral etiology, were treated with Ribavirin as per Example 1. The four pharyngotonsillitis patients showed rapid remission of the clinical cessation of respiratory stress in 12 hours, remission of hyperthermia and coughing in 36 hours, and abatement of symptoms in 72 hours.

EXAMPLE 4

Rubeola (Measles)

Using a double-blind placebo controlled protcol 20 patients ages 1 to 12 years diagnosed as having measles were divided into a placebo group. Clinical parameters used to evaluate the treatment were: fever, exanthem, cough, rhinorrhea, and malaise. Symptoms were graded 0 through 4 wherein zero was absence of symptoms and 4 was the highest severity observed. The drug control group received Ribavirin at a dosage of 10 mg/kg of body weight/day/for 7 days. A statistical significant difference in both duration of disease and severity of symptoms was observed between the drug treated group and the placebo group.

Mean symptom score of all patients in drum treated group and placebo group and percent of patient having a score of one or greater per day.

Mean symptom score of all patients in drug treated group and placebo group and percent of patient having a score at one or greater per day.

| | | DAY | | | | | | | |
|---|---|---|---|---|---|---|---|---|---|
| | | 0 | 1 | 2 | 3 | 4 | 5 | 6 | 7 |
| Cough | Drug mean score | 3.3 | 2.3 | 1.8 | 1.1 | .7 | .1 | .1 | .1 |
| | Placebo mean score | 2.8 | 2.8 | 2.7 | 2.2 | 2.4 | 2.3 | 1.8 | 1.5 |
| | Drugs % with symptoms | 100 | 100 | 90 | 80 | 70 | 10 | 10 | 10 |
| | Placebo % with symptoms | 100 | 100 | 89 | 78 | 89 | 78 | 78 | 78 |
| Fever | Drug mean score | 3.3 | 2.3 | 1.2 | .3 | .1 | 0 | 0 | 0 |
| | Placebo mean score | 3.4 | 3.8 | 3.3 | 1.6 | 1.6 | 1.3 | .9 | .6 |
| | Drug % with symptoms | 90 | 80 | 60 | 30 | 10 | 0 | | |
| | Placebo % with symptoms | 100 | 100 | 100 | 100 | 78 | 67 | 44 | 33 |
| Exantham | Drug mean score | 1.7 | 3.0 | 1.4 | .2 | 0 | | | |
| | Placebo mean score | 1.1 | 2.6 | 3.2 | 2.3 | 1.4 | .7 | .4 | .2 |
| | Drug % with symptoms | 70 | 100 | 70 | 20 | 0 | | | |
| | Placebo % with symptoms | 67 | 89 | 100 | 100 | 78 | 33 | 11 | 11 |
| Rhinorrhea | Drug means score | 2.9 | 1.6 | .7 | .3 | .1 | 0 | | |
| | Placebo mean score | 3.3 | 3.2 | 2.8 | 1.8 | 1.4 | 1.2 | 1.0 | .8 |
| | Drug % with symptoms | 90 | 70 | 50 | 30 | 10 | 0 | | |
| | Placebo % with symptoms | 100 | 100 | 100 | 78 | 78 | 78 | 67 | 67 |
| Malaise | Drug mean score | 3.6 | 2.4 | 1.4 | .6 | .1 | 0 | | |
| | Placebo mean score | 3.8 | 3.7 | 3.4 | 3.1 | 2.7 | 2.2 | 1.1 | .9 |
| | Drug % with symptoms | 100 | 90 | 70 | 50 | 10 | 0 | | |
| | Placebo % with symptoms | 100 | 100 | 100 | 100 | 100 | 100 | 67 | 67 |
| * | Patient dropped out from study on second day of observation | | | | | | | | |

EXAMPLE 5

Herpes Zoster

A. Topical Treatment

Sixteen patients with an initial illness consisting of various neoplastic diseases and secondary herpes zoster were randomly assigned into placebo and Ribavirin treated groups. Neither patient nor treating physician were aware of these assignments during the study. A topical ointment containing 5% Ribavirin was used. The placebo received the same ointment but without the added drug. Ointment was applied twice daily for 8 days. Criterion for evaluation of effectiveness of therapy was duration of the zoster illness as determined by length of pain and lesions.

The placebo group showed a 5½ days average length of lesion and an 8½ days average length of pain. The Ribavirin group showed a significant reduction of averge length of both lesion and pain to 5½ days and 2½ days, respectively.

B. Oral and Intravenous Treatment

Eighteen patients with herpes zoster were divided into three groups, four were treated with Ribavirin 400 mg/day (100 g.i.d.) given oraly for 8 days, ten were treated with Ribavirin 400 mg/day (200 mg b.i.d.) for 8 days and four were analgesics and/or some other medication, i.e., one patient received Darvon and aspirin, one patient received Dipirone and Vitamin $B_{12}$ and two patients received Dipirone Criterian for evaluation of therapy against the illness was evaluated by:
  a. duration of the disease in days,
  b. duration of the pain in days,
  c. beginning of involution of the lesions present in days
  d. Beginning of the decay at the scabs in days.

Both in oral and intravenous therapy showed statistically significant effectiveness as compared to the group not treated with Ribavirin.

| | Analysis of Results | | | |
|---|---|---|---|---|
| Patient Number | Duration of Disease (Days) | Duration of Pain (Days) | Beginning of Involution of Lesions (Days) | Beginning of Decay of Scabs (Days) |
| Control Group | | | | |
| 1 | 6 | 8 | 8 | 12 |
| 2 | 8 | 8 | 7 | 10 |
| 3 | 4 | 6 | 3 | 6 |
| 4 | 10 | 10 | 10 | 12 |
| Mean | 7 | 8 | 7 | 10 |
| Oral Ribavirin | | | | |
| 5 | 4 | 6 | 2 | 4 |
| 6 | 4 | 6 | 2 | 6 |
| 7 | 5 | 6 | 3 | 5 |
| 8 | 3 | 2 | 3 | 8 |
| Mean | 4 | 5 | 2.6 | 5.75 |
| Intravenous Ribavirin | | | | |
| 9 | 3 | 5 | 3 | 5 |
| 10 | 6 | 2 | 2 | 5 |
| 11 | 2 | — | 1 | 2 |
| 12 | 4 | 2 | 2 | 3 |
| 13 | 7 | 1 | 2 | 6 |
| 14 | 2 | 1 | 3 | 5 |
| 15 | 3 | 1 | 3 | 6 |
| 16 | 3 | 2 | 3 | 6 |
| 17 | 3 | 2 | 4 | 6 |
| 18 | 10 | 2 | 3 | 4 |
| Mean | 4.3 | 2.0 | 2.5 | 4.8 |
| Summary of Mean and Statistical evaluation of students to test | | | | |
| Control | 7 | 8 | 7 | 10 |
| Oral Ribavirin | 4 | 5 | 2.6 ($p<0.01$) | 5.75 ($p<0.05$) |
| Intravenous Ribavirin | 4.3 | 2 ($p<0.001$) | 2.5 ($p<0.05$) | 4.8 ($p<0.001$) |

EXAMPLE 6

Gastroenteritis

A patient, 6 months of age, with gastroenteritis did not respond to the usual treatment. Therefore, the disease was suspected to be of viral origin. The patient was treated with 100 mg of Ribavirin every 24 hours. Symptoms diminished within 24 hours after the beginning of Ribavirin treatment.

EXAMPLE 7

Mulluscum Contagiosum

Three patients aged 2 to 5 years with mulluscum contagiosum were treated with Ribavirin as per Example 1 with good results.

EXAMPLE 8

Herpes Gingivostomatitis

Twenty patients diagnosed as having herpes gingivostomatitis were treated using a double-blind placebo controlled protocol. Ten patients were treated with Ribavirin 400 mg/day (100 mg g.i.d.) for 5 days orally and ten patients were treated with placebo g.i.d. The patients were evaluated for severity and duration of pain, ulcers, adenopathy and difficulty in speaking and swallowing. Comparison of the duration in days of the mean of all patients in each group showed a statistically significant difference in both duration of pain and ulcers for the drug treated group.

| Mean Duration in Days | | | Difficulty in | | |
|---|---|---|---|---|---|
| Patient Group | Pain | Ulcers | Speaking | Swallowing | Adenopathy |
| Placebo | 4.4 | 5.3 | 3.1 | 2.8 | 3.1 |
| Ribavirin | 2.7 (P 0.05)[a] | 3.4(p 0.01)[a] | 2.9 | 2.2 | 2.8 |

[a] Students t test

EXAMPLE 9

Meningo-encephalitis

A patient 18 months old with meningo-encephalitis complicated with viral pneumonitis was treated with Ribavirin as per Example 1 for a period of 7 days. Remission of the respiratory condition was observed in 24 hours and recuperation of alertness, with the disappearance of neurological signs was noted 48 hours later. A second patient 3 years in age with less severe clinical signs responded following 2 days of treatment. Treatment was continued for 5 days.

EXAMPLE 10

Influenza B

Thirty male volunteers, all of whom lacked serum neutralizing antibodies against the challenged Type B influenza virus, were divided into drug and placebo groups using a double blind protocol. The drug control group received Ribavirin in 200 mg doses three times per day. The placebo group received placebo capsules three times per day. After subjects were examined by a physician once a day and graded for signs and symptoms on a scale of 0 to 3+, with 0 being not present, 1+ mild, 2+ moderate, and 3+ severe. Most of the signs and symptoms occurred in both the Ribavirin-treated and placebo-treated groups. However, the scores of some of the constitutional symptoms, i.e., feverishness, sweating, malaise, joint and muscle pains, and others, and of the respiratory symptoms and nasal mucosal changes were generally lower in the drug-treated subjects. Total sign and symptom scores by day for the two groups indicate that scores for the Ribavirin-treated group were consistently lower.

Distribution of Ribavirin-treated and Placebo-treated Subjects in Four Classes of Influenza Illness with Different Severity

| Illness Score | Ribavirin-treated Subject | Placebo-treated Subject |
|---|---|---|
| 3+ | 1 | 5 |
| 2+ | 2 | 3 |
| 1+ | 7 | 2 |
| 0 | 5 | 5 |
|  | 15 | 15 |

Difference in Daily Total Illness Scores Between Ribavirin-treated and Placebo-treated Groups Day Post-challenge

| −1 | 0 | 1 | 2 | 3 | 4 | 5 | 6 | 7 | 8 |
|---|---|---|---|---|---|---|---|---|---|
| Ribavirin-treated Group | | | | | | | | | |
| 0 | 0 | 5 | 194 | 191 | 160 | 82 | 13 | 0 | 1 |
| Placebo-treated Group | | | | | | | | | |
| 1 | 1 | 28 | 319 | 312 | 279 | 115 | 29 | 3 | 0 |

Virus titer isolation from nasal washings from both groups up to 8 days post-challenge was almost identical. No drug-related side effects were observed.

EXAMPLE 11

Influenza $A_2$

Ribavirin treatment was used in a double blind study during an influenza outbreak in a closed boarding school population of sixty-one girls aged 8 to 16 years. Six groups were selected from the overall population, each group consisting of eight individuals randomly selected as symptoms of influenza were first reported. Patients in which the infection had already become well-established were not used. Three groups were treated with Ribavirin 100 mg three times per day and three groups with placebo capsules three times per day. The virus was identified as influenza $A_2$/England from throat washings taken at the onset of the disease. Subjective symptoms were obtained through direct questions to the patients. The degree of severity of clinical signs of illness was greater for placebo-treated as compared to Ribavirin-treated as seen by the following summary.

Distribution of Clinical Signs of Influenza in

Patients Treated with Placebo or Ribavirin
Degree of Severity* (No. of Patients)

| Clinical Sign | Mild | | Moderate | | Severe | |
|---|---|---|---|---|---|---|
|  | Placebo | Drug | Placebo | Drug | Placebo | Drug |
| Fever | 6 | 0 | 14 | 0 | 4 | 0 |
| Malaise | 6 | 2 | 14 | 2 | 4 | 0 |
| Rhinitis (cough) | 4 | 3 | 4 | 1 | 16 | 2 |
| Pharyngitis | 3 | 2 | 21 | 3 | 0 | 2 |
| Gastroenteritis | 0 | 0 | 0 | 0 | 0 | 0 |
| Headache | 3 | 1 | 19 | 2 | 2 | 0 |
| Myalgia | 15 | 0 | 0 | 3 | 0 | 0 |
| Conjunctivitis | 5 | 0 | 11 | 2 | 0 | 1 |

*Composite of determinations made beginning 24 hours after initiation of therapy.

Summary of Influenza Illness Distribution Among Patients Treated with Placebo or Ribavirin

| Degree of Illness | Placebo-treated | Ribavirin-treated |
|---|---|---|
| Severe | 16 | 2 |
| Moderate | 4 | 1 |
| Mild | 4 | 3 |
| Absent | 0 | 15 |

EXAMPLE 12

Influenza A

Using a double-blind placebo control protocol, thirty volunteers were given an Influenza A, Victoria ($H_3N_2$) challenge. One patient developed an allergic complication to the challenge and was dropped. The remaining patients (15 in placebo group and 14 in drug group) were medicated with Ribavirin 1000 mg/day in divided doses three times per day or identical leveling placebo capsules.

The efficacy of the drug was evaluated by:

A. Symptoms: wherein the patients indication of feeling of eyes, ears, nose, throat, lymph nodes, trachea, larnyx, chest, gastro-intestinal system, skin and general systemic response was graded. The severity was graded on a 0–3 basis with each site having 2 to 5 parameters to be considered.

B. Signs: wherein the Physician assigned a severity score of 0–3 based on the physical signs observed at the above indicated sites. Temperatures were also a part of the physical sign record.

C. Physcians opinion: wherein after observing the physical signs, and recording the symptoms, the physician then assigned a severity score of 0–3 to the following categories not ill, rhinitis, pharyngitis, tracheobronchitis, pneumonia, systemic, or other.

D. Nasal virus isolates: wherein nasal washes were performed daily from days 1–7 to determine the number of patients shedding virus and concentration of that virus.

E. Serum Antibody: wherein blood was drawn at several in intervals to determine the number of patients developing antibody and the concentration of the antibody.

The challenge inoculum was chosen such that all volunteers were expected to contract the induced viral disease and to recover from the induced viral disease. The effectiveness of the drug was measured by the reaction in the severity of the induced disease in the drug treated group compared to the placebo treated group.

Comparison of disease severity of influenza infected drug and placebo treated groups showed:

|  | Group | Mean* Total Scores | Ratio (Placebo/ Drug) |
|---|---|---|---|
| Symptoms | Placebo | 26.6 | 2.4:1 |
|  | Drug | 11.1 |  |
| Signs | Placebo | 9.9 | 1.7:1 |
|  | Drug | 5.9 |  |
| Physician's opinion scores | Placebo | 8.1 | 2.3:1 |
|  | Drug | 3.5 |  |

(*Group means were determined after totaling daily scores for all subjects).

Comparison of duration of disease parameters in influenza infected drug and placebo treated groups showed:

|  | Group | No. Subjects | Total days | mean |
|---|---|---|---|---|
| Symptom Scores | ≧5 Placebo | 8 | 23 | 2.9 |
|  | drug | 5 | 8 | 1.6 ($p<0.05$)a |
| Signs Scores | ≧3 Placebo | 6 | 18 | 3.0 |
|  | drug | 3 | 8 | $1.6^b$ |
| Physician Opinion Scores | ≧3 Placebo | 7 | 15 |  |
|  | Drug | 2 ($p<0.05$)$^c$ | 3 (p 0.05) | $1.5^b$ |
| Temperatures | ≧$100.0^d$ Placebo | 5 | 12 | 2.4 |
|  | Drug | 0 ($p<0.05$)$^c$ | 0 | $0^b$ |

$^a$Mean evaluation by t test
$^b$Insufficient numbers for mean evaluation t Test
$^c$Numbers evaluation by Fisher's exact test or chi wquare analysis
$^d$only 8 am and 8 pm temperatures compared.

Comparison of mean nasal virus titers (mean of positive samples) of influenza infected drug and placebo treated groups showed:

| Group | VIRUS TITERS ($Log_{10}$) Days | | | | | | |
|---|---|---|---|---|---|---|---|
|  | 1 | 2 | 3 | 4 | 5 | 6 | 7 |
| Placebo | $1.5^a$ | 3.1 | 2.2 | 2.6 | 2.2 | 2.0 | 2.4 |
| Drug | 0.9 | 2.0 | 1.8 | 1.4 | 0.9 ($p <0.05$)$^b$ | 1.3 | 2.6 |

$^a$Mean of positive samples
$^b$Statistical evaluation by t test

Comparison of the number of isolates and the number of titers $10^3$ of influenza infected drug and placebo treated groups showed:

| Group | No. Subjects Positive | No. Samples$^a$ Positive | No. Samples Titers $10^3$ |
|---|---|---|---|
| Placebo | 11 | 38 | 12 |
| Drug | 9 | 30 | 4 ($p <0.05$)$^b$ |

$^a$105 total samples in placebo group and 98 in the ribavirin group
$^b$Statistical evaluation by Chi square Comparison of the subjects exhibiting a ≧4 fold rise in antibody titer of influenza infected drug and placebo treated groups showed:

| Group | No. Subjects | Final Titer |
|---|---|---|
| Placebo | 8 | 22 |
| Drug | 8 | 21 |

The total days of moderate to severe symptoms and signs in the drug treated group were significantly less than those of the placebo group, and the total days with at least one temperature of 100° F. or greater were significantly lower in the virus treated group compared to the placebo group.

That consistently higher concentrations of virus were detected in nasal washes from Placebo subjects than from Ribavirin treated subjects. In addition more virus isolations and titers $10^3$ were observed from Placebo samples than Ribavirin treated samples.

That both groups exhibited comparable rates and degrees of antibody production.

EXAMPLE 13

Herpes Labialis

Seventeen patients between the ages of 1 and 7 years with Herpes labialis were treated as per Example 1. Satisfactory remission of symptoms were observed by the second or third day of treatment. Recurrence of symptoms occurred in two patients.

EXAMPLE 14

Acute Viral Hepatitis

Eight patients between the ages of 2 and 14 years were treated as per Example 1. Treatment considerably curtailed the development of symptoms with normalization of the transaminases in 3 to 4 days and remission of the clinical symptoms in 5 to 8 days.

In a second study, sixty-six patients with the clinical diagnosis of acute viral hepatitis were divided into two groups and treated using a double blind protocol with either a 0.25 g placebo capsule or a 0.25 g capsule containing 0.10 g of Ribavirin every 6 hours. The published results of this study, i.e., Action of 1-B-D-ribofuranosyl-1,2,4-triazole-3-carboxamide (Ribavirin) on Acute Viral Hepatitis, Paulo Augusto Ayrosa Galvao, Ann. N.Y. Acad. Sci., 284, 278 (1977) are herein expressly incorporated by reference. The study can be summarized as follows:

The effect of Ribavirin was evaluated by the clinical picture and by the changes in both direct and total serum bilirubin and in the activity of serum glutamic pyruvic (SGPT) and glutamic oxalo-acetic (SGOT) transaminases. There was a statistically significant decrease in serum bilirubin, SGOT and SGPT from the 5th to the 10th day of treatment for the Ribavirin-treated group. The decrease noted for the placebo group was not statistically significant.

EXAMPLE 15

Herpes Progenitalis

Fifty patients having severe, recurrent herpes progenitalis of a duration of at least one year and a minimum of 4 to 6 episodes during the previous 12 months were evaluated using a double-blind placebo protocol. The drug treated patients were given Ribavirin at 800 mg/day (200 mg g.i.d.) for 10 days. This course of treatment was repeated a second and third time in certain instances. After the first course of treatment 18 patients did not return for a second treatment and of the 30 patients in this phase of the study, 15 patients dropped out from a third course of treatment. On telephone follow-up most reported no recurrence and a few could not be contacted. Patients were usually seen within 24 hours of onset of lesions to confirm clinical diagnosis and for routine blood and urine tests. Once treatment was initiated patients were seen every other day. Patient's response was recorded noting features such as pain, new vesicles, old vesicles, erythema and edema and ulcers. Pain response to treatment was scored 0 to 4; new vesicles and old vesicles response to treatment was scored 0 to 2, erythema and edema and ulcers response to treatment was scored 0 to 3. Zero was always no response and the higher number corresponded to best response to ribavirin's therapy.

When the study was completed, individual codes were broken and the patients assigned to drug or placebo groups. The weighted score for each patient and for each course of treatment were evaluated separately for each therapeutic trail. Where patient results could be followed through one, two or three courses of treatment, ribavirin consistently showed a highly statistically significant (P=0.001) diminution of duration of disease and severity of signs and symptoms as compared to the placebo group. Recurrences were observed in both groups, but because some patients could not be followed to the completion of the study, no definitive conclusions are drawn with regard to ribavirin's efficacy in preventing recurrences or in diminishing the frequency and severity of such recurrences.

All of the scores of the patients in each group were added together and the mean score determined. The following table shows these mean patient scores and also the study t value and probability of this value for day 3–10.

|  | Ribavirin Day | | | | Placebo Day | | | |
|---|---|---|---|---|---|---|---|---|
|  | 3 | 5 | 7 | 10 | 3 | 5 | 7 | 10 |
| First Treatment | | | | | | | | |
| Ulcers | | | | | | | | |
| Mean | 1.6 | 1.9 | 2.5 | 2.6 | 1.7 | 2.0 | 2.0 | 2.0 |
| t-value |  | 4.5 ($P<0.001$) |  |  |  | 1.2 ($P<0.2$) |  |  |
| Erythema and Edema | | | | | | | | |
| Mean | 1.4 | 1.7 | 2.2 | 2.3 | 1.7 | 1.9 | 1.7 | 1.8 |
| t-value |  | 4.7 ($P<0.001$) |  |  |  | .4 ($P<0.8$) |  |  |
| Old Vesicles | | | | | | | | |
| Mean | .9 | 1.2 | 1.6 | 1.8 | .9 | 1.2 | 1.1 | 1.1 |
| t-value |  | 7.1 ($P<0.001$) |  |  |  | 1.4 ($P<0.2$) |  |  |
| New Vesicles | | | | | | | | |
| Mean | 1.1 | 1.2 | 1.6 | 1.8 | 1.6 | 1.7 | 1.7 | 1.7 |
| t-value |  | 5.0 ($P<0.001$) |  |  |  | .8 ($P<0.5$) |  |  |
| Degree of Pain | | | | | | | | |
| Mean | 2.8 | 3.0 | 3.7 | 3.7 | 2.7 | 2.9 | 2.9 | 2.9 |
| t-value |  | 4.8 ($P<0.02$) |  |  |  | 0.5 ($P<0.8$) |  |  |
| Second Treatment | | | | | | | | |
| Ulcers | | | | | | | | |
| Mean | 2.1 | 2.4 | 2.9 | 3.0 | 1.9 | 2.1 | 2.1 | 2.2 |
| t-value |  | 4.8 ($P<0.001$) |  |  |  | .9 ($P<0.5$) |  |  |
| Erythema and Edema | | | | | | | | |
| Mean | 1.4 | 1.6 | 2.1 | 2.4 | 1.2 | 1.4 | 1.4 | 1.4 |
| t-value |  | 3.8 ($P<0.001$) |  |  |  | .6 ($P<0.8$) |  |  |
| Old Vesicles | | | | | | | | |
| Mean | 1.1 | 1.3 | 1.9 | 1.9 | 1.1 | 1.3 | 1.3 | 1.3 |
| t-value |  | 4.1 ($P<0.001$) |  |  |  | .8 ($P<0.5$) |  |  |
| New Vesicles | | | | | | | | |
| Mean | 1.4 | 1.8 | 1.9 | 2.0 | 1.6 | 1.7 | 1.1 | 1.3 |
| t-value |  | 4.6 ($P<0.001$) |  |  |  | .98 ($P<0.5$) |  |  |
| Degree of Pain | | | | | | | | |
| Mean | 2.8 | 3.3 | 3.7 | 4.0 | 3.0 | 3.4 | 3.5 | 3.6 |
| t-value |  | 4.9 ($P<0.001$) |  |  |  | 2.1 ($P<0.05$) |  |  |
| Third Treatment | | | | | | | | |
| Ulcers | | | | | | | | |
| Mean | 1.7 | 2.2 | 2.7 | 2.8 | 1.7 | 2.0 | 1.9 | 1.7 |
| t-value |  | 4.0 ($P<0.001$) |  |  |  | 0 |  |  |
| Erthema and Edema | | | | | | | | |
| Mean | 1.8 | 2.2 | 2.3 | 2.3 | 2.1 | 1.7 | 1.1 | 1.1 |
| t-value |  | 2.0 ($P<0.05$) |  |  |  | 2.3 ($P<0.05$) |  |  |
| Old Vesicles | | | | | | | | |
| Mean | 1.4 | 1.7 | 1.8 | 1.8 | 1.4 | 1.4 | 1.1 | 1.4 |
| t-value |  | 1.5 ($P<0.1$) |  |  |  | .7 ($P<0.5$) |  |  |

-continued

| | Ribavirin Day | | | | Placebo Day | | | |
|---|---|---|---|---|---|---|---|---|
| | 3 | 5 | 7 | 10 | 3 | 5 | 7 | 10 |
| New Vesicles | | | | | | | | |
| Mean | 1.3 | 1.7 | 2.0 | 1.8 | 1.9 | 1.7 | 1.7 | 1.7 |
| t-value | | .28 ($P<0.02$) | | | | .4 ($P<0.8$) | | |
| Degree of Pain | | | | | | | | |
| Mean | 2.7 | 3.2 | 3.6 | 3.8 | 2.8 | 3.3 | 3.0 | 3.0 |
| t-value | | 2.7 ($P<0.02$) | | | | .37 ($P<0.8$) | | |

Evidence has implicated a measles-like virus with the demyelinating diseases of multiple sclerosis and subacute sclerosing panencephalitis. Progressive multifocal encephalopthy is associated with a human papovaviruses.

In Sjogren Syndrome, systemic lupus erythematosus, and rheumatoid arthritis physical damage is caused by auto-immune response however, certain evidence, including the discovery of viral-like inclusions, suggest that the virus might be the primary cause of these diseases.

Rubella virus is teratogenic and if a mother is infected during the first trimester of pregnancy, there is a high chance that birth defects will result. Transient arthritis is also seen following rubella or vaccination with certain rubella vaccines.

1-B-D-ribofuranosyl-1,2,4-triazole-3-carboxamide has been given to terminally ill patients, in a tolerance study. Does up to 26 2600 milligrams per square meter ($mg/m^2$)tid (equal to 12,600 mg/day) three times per day have been tolerated. This high dose produced an anemia which was reversible upon withdrawal of the drug.

We claim:

1. A process of treating viral diseases in humans which comprises administering to the human patients an antiviral agent which has as its active component the compound 1-B-D-ribofuranosyl-1,2,4-trazole-3-carboaxmide.

2. A process of treating viral diseases in humans which are caused by poxviruses, herpes viruses, othomyxoviruses or paramyxoviruses which comprises administering to the human patients an antiviral agent which has as its active component the compound 1-B-D-ribofuranosyl-1,2,4-triazole-3-carboxamide.

3. The process of claim 2 wherein the viral disease is caused by a member of the poxviruses.

4. The process of claim 2 wherein the viral disease is caused by a member of the herpesviruses.

5. The process of claim 2 wherein the viral disease is caused by a member of the othomyxoviruses.

6. The process of claim 2 wherein the viral disease is caused by a member of theparamyxoviruses.

7. A process of treating viral diseases in humans comprising administering to the human patients an effective amount of a composition containing from about 0.01% to 50% by weight, based on the total weight of the composition, of the compound 1-B-D-ribofuranosyl-1,2,4-triazole-3-carboxamide.

8. A process of treating viral diseases in humans which are caused by poxviruses, herpes viruses, othomyxoviruses or paramyxoviruses comprising administering to the human patient an effective amount of a composition contianing from about 0.01% to 50% by weight, based on the total weight of the composition of the compound 1-B-D-ribofuranosyl-1,2,4-triazole-3-carboxamide.

9. The process of claim 8 wherein the composition is administered orally.

10. The process of claim 8 wherein the composition is administered topically.

11. The process of claim 8 wherein the composition is administered by injection.

12. The process of claim 8 wherein the composition is administered via the respitory tract.

13. The process of claim 8 wherein the composition is administered ophthalmically.

14. A process for treating viral hepatitis in humans which comprieses administering to a patient an oral preparation containing as its active ingredient the compound 1-B-D-ribofuranosyl 1,2,4-triazole-3-carboxamide in a total daily dose of approximately 100 to 1000 milligrams of the compound.

15. The process of claim 5 for treating influenza in humans which comprises administering to a patient a composition containing as its active ingredient the compound 1-B-D-ribofuranosyl-1,2,4-triazole-3-carboxamide in a total daily dose of approximately 100 to 1000 milligrams of the compound.

16. The process of claim 15 wherein the composition is administered orally.

17. The process of claim 4 of treating herpes labialis, herpes progenitalis, herpes zoster, and herpes gingivostomatitis in humans which comprises administering to a patient a composition containing as its active ingredient the compound 1-B-D-ribofuranosyl-1,2,4-triazole-3-carboxamide.

18. The process of claim 17 wherein the composition is administered orally in a total daily dose of approximately 100 to 1000 milligrams of the compound.

19. The process of claim 17 wherein the composition is a topical composition containing from about 0.5% to 5% of the compound.

20. A process for treating measles in humans which comprises administering to a patient a composition containing as its active ingredient the compound 1-B-D-ribofuranosyl-1,2,4-triazole-3-carboxamide, in a total daily dose of approximately 100 to 1000 milligrams of the compound.

* * * * *

UNITED STATES PATENT AND TRADEMARK OFFICE
CERTIFICATE OF CORRECTION

PATENT NO. : 4,211,771
DATED : July 8, 1980
INVENTOR(S) : Joseph T. Witkowski and Roland K. Robins It is certified that error appears in the above-identified patent and that said Letters Patent are hereby corrected as shown below:

At col. 1, line 54, after "cytarabine" remove --(cytarabine --;
At col. 2, line 4, read "and" as --an--;
At col. 11, line 11, read "Dipirone Criterian" as --Dipirone. Criteria--;
In col. 12, the portion of the table at lines 52 through 55 should read continuous with the portion of the table at lines 17 through 20;
At col. 14, line 34, read "leveling" as --looking--;
In col. 15, in the table spanning lines 15 through 33, read the left hand portion of the table as
--

|  | Group |
|---|---|
| Sympton Scores $\geq 5$ | Placebo<br>Drug |
| Signs Scores $\geq 3$ | Placebo<br>Drug |
| Physician Opinion Scores $\geq 3$ | Placebo<br>Drug |
| Temperature $\geq 100.0^d$ | Placebo<br>Drug |

--;

In col 15, line 30 in footnote c, read "wquare" as --square--;
At col. 19, line 32, after "to" delete --26--;

UNITED STATES PATENT AND TRADEMARK OFFICE
CERTIFICATE OF CORRECTION

PATENT NO. : 4,211,771

DATED : July 8, 1980

INVENTOR(S) : Joseph T. Witkowski and Roland K. Robins

It is certified that error appears in the above-identified patent and that said Letters Patent are hereby corrected as shown below:

At col.19, line 56, read "theparamyxoviruses" as --the paramyxoviruses--;

At col. 1, line 62; col. 2, lines 1, 5 and 14; col. 3, line 39 col 4, lines 7 and 52; col. 5, lines 26, 40 and 53; col. 6, lines 16 and 23; col. 8, lines 5, 38 and 48; col. 19, lines 30, 42, 48 and 62 col. 20, lines 19, 33, 48 and 58; read 1-B-D-etc as --1-β-D-etc--;

In the title and the abstract, read 1-B-D-etc as --1-β-D-etc--.

Signed and Sealed this

Twenty-eighth Day of April 1981

[SEAL]

Attest:

RENE D. TEGTMEYER

Attesting Officer

Acting Commissioner of Patents and Trademarks

UNITED STATES PATENT AND TRADEMARK OFFICE

CERTIFICATE EXTENDING PATENT TERM
UNDER 35 U.S.C. 156

Patent No.    : 4,211,771

Dated         : July 8, 1980

Inventor(s)   : Joseph T. Witkowski, et al

Patent Owner  : Viratek, Inc.

This is to certify that there has been presented to the

COMMISSIONER OF PATENTS AND TRADEMARKS an application under 35 U.S.C. 156 for an extension of the patent term. Since it appears that the requirements of law have been met, this certificate extends the term of the patent for the period of

2 YEARS with all rights pertaining thereto as provided by 35 USC 156(b).

I have caused the seal of the Patent and Trademark Office to be affixed this Nineteenth day of December 1986.

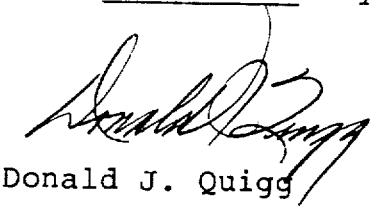

Donald J. Quigg

Assistant Secretary and Commissioner of Patents and Trademarks